(12) United States Patent
Ritter et al.

(10) Patent No.: US 7,708,696 B2
(45) Date of Patent: May 4, 2010

(54) NAVIGATION USING SENSED PHYSIOLOGICAL DATA AS FEEDBACK

(75) Inventors: Rogers C. Ritter, Charlottesville, VA (US); Raju R. Viswanathan, St. Louis, MO (US)

(73) Assignee: Stereotaxis, Inc., St. Louis, MO (US)

( * ) Notice: Subject to any disclaimer, the term of this patent is extended or adjusted under 35 U.S.C. 154(b) by 1004 days.

(21) Appl. No.: 11/329,957

(22) Filed: Jan. 11, 2006

(65) Prior Publication Data

US 2006/0270915 A1 Nov. 30, 2006

Related U.S. Application Data

(60) Provisional application No. 60/642,853, filed on Jan. 11, 2005.

(51) Int. Cl.
*A61B 5/02* (2006.01)
(52) U.S. Cl. ...................................... 600/508
(58) Field of Classification Search ................. 600/374, 600/393, 424, 373; 606/32, 41; 607/101, 607/113, 98–99, 148, 122, 41, 116, 125–128, 607/9, 14
See application file for complete search history.

(56) References Cited

U.S. PATENT DOCUMENTS

| | | | |
|---|---|---|---|
| 5,654,864 A | 8/1997 | Ritter et al. | |
| 5,657,755 A * | 8/1997 | Desai ......................... | 600/374 |
| 5,931,818 A | 8/1999 | Werp et al. | |
| 6,014,580 A | 1/2000 | Blume et al. | |
| 6,015,414 A | 1/2000 | Werp et al. | |
| 6,128,174 A | 10/2000 | Ritter et al. | |
| 6,148,823 A | 11/2000 | Hastings | |
| 6,152,933 A | 11/2000 | Werp et al. | |
| 6,157,853 A | 12/2000 | Blume et al. | |
| 6,212,419 B1 | 4/2001 | Blume et al. | |
| 6,241,671 B1 | 6/2001 | Ritter et al. | |
| 6,292,678 B1 | 9/2001 | Hall et al. | |
| 6,296,604 B1 | 10/2001 | Garibaldi et al. | |
| 6,298,257 B1 | 10/2001 | Hall et al. | |
| 6,304,768 B1 | 10/2001 | Blume et al. | |
| 6,315,709 B1 | 11/2001 | Garibaldi et al. | |

(Continued)

OTHER PUBLICATIONS

International Search Written and Written Opinion Dated: Aug. 15, 2007 pp. 9.

*Primary Examiner*—George Manuel
*Assistant Examiner*—Robert N Wieland
(74) *Attorney, Agent, or Firm*—Harness, Dickey & Pierce, P.L.C.

(57) ABSTRACT

A method for controlling a remote navigation system includes operating the remote navigation system to bring a sensor carried on a medical device successively into a plurality of locations in a predetermined pattern, and using the sensor to sense a physiological property in each location. At least once thereafter, the remote navigation system is operated to bring a sensor carried on a medical device successively into a series of locations in a predetermined pattern relative to at least one location selected from the predetermined pattern in the immediately preceding step based upon the sensed physiological property value, and uses the sensor to sense the physiological property in each location. A local extreme value of the sensed physiological property is thereby located. The physiological properties that can be sensed include electrical signals, conductivity, temperature, fluid flow rate or fluid velocity, and range of motion of a surface.

15 Claims, 3 Drawing Sheets

U.S. PATENT DOCUMENTS

| | | |
|---|---|---|
| 6,330,467 B1 | 12/2001 | Creighton, IV et al. |
| 6,352,363 B1 | 3/2002 | Munger et al. |
| 6,364,823 B1 | 4/2002 | Garibaldi et al. |
| 6,375,606 B1 | 4/2002 | Garibaldi et al. |
| 6,385,472 B1 | 5/2002 | Hall et al. |
| 6,401,723 B1 | 6/2002 | Garibaldi et al. |
| 6,428,551 B1 | 8/2002 | Hall et al. |
| 6,459,924 B1 | 10/2002 | Creighton, IV et al. |
| 6,475,223 B1 | 11/2002 | Werp et al. |
| 6,505,062 B1 | 1/2003 | Ritter et al. |
| 6,507,751 B2 | 1/2003 | Blume et al. |
| 6,522,909 B1 | 2/2003 | Garibaldi et al. |
| 6,524,303 B1 | 2/2003 | Garibaldi |
| 6,527,782 B2 | 3/2003 | Hogg et al. |
| 6,537,196 B1 | 3/2003 | Creighton, IV et al. |
| 6,542,766 B2 | 4/2003 | Hall et al. |
| 6,562,019 B1 | 5/2003 | Sell |
| 6,574,492 B1* | 6/2003 | Ben-Haim et al. .......... 600/374 |
| 6,630,879 B1 | 10/2003 | Creighton, IV et al. |
| 6,662,034 B2 | 12/2003 | Segner et al. |
| 6,677,752 B1 | 1/2004 | Creighton, IV et al. |
| 6,702,804 B1 | 3/2004 | Ritter et al. |
| 6,733,511 B2 | 5/2004 | Hall et al. |
| 6,755,816 B2 | 6/2004 | Ritter et al. |
| 6,817,364 B2 | 11/2004 | Garibaldi et al. |
| 6,834,201 B2 | 12/2004 | Gillies et al. |
| 6,902,528 B1 | 6/2005 | Garibaldi et al. |
| 6,911,026 B1 | 6/2005 | Hall et al. |
| 6,940,379 B2 | 9/2005 | Creighton |
| 6,968,846 B2 | 11/2005 | Viswanathan |
| 6,975,197 B2 | 12/2005 | Creighton, IV |
| 6,980,843 B2 | 12/2005 | Eng et al. |
| 7,008,418 B2 | 3/2006 | Hall et al. |
| 7,010,338 B2 | 3/2006 | Ritter et al. |
| 7,019,610 B2 | 3/2006 | Creighton, IV et al. |
| 7,020,512 B2 | 3/2006 | Ritter et al. |
| 7,066,924 B1 | 6/2006 | Garibaldi et al. |
| 7,137,976 B2 | 11/2006 | Ritter et al. |
| 7,161,453 B2 | 1/2007 | Creighton, IV |
| 7,189,198 B2 | 3/2007 | Harburn et al. |
| 7,190,819 B2 | 3/2007 | Viswanathan |
| 7,211,082 B2 | 5/2007 | Hall et al |
| 7,248,914 B2 | 7/2007 | Hastings et al. |
| 7,264,584 B2 | 9/2007 | Ritter et al. |
| 2001/0038683 A1 | 11/2001 | Ritter et al. |
| 2002/0019644 A1 | 2/2002 | Hastings et al. |
| 2002/0100486 A1 | 8/2002 | Creighton, IV et al. |
| 2002/0177789 A1 | 11/2002 | Ferry et al. |
| 2003/0125752 A1 | 7/2003 | Werp et al. |
| 2004/0006301 A1 | 1/2004 | Sell et al. |
| 2004/0019447 A1 | 1/2004 | Shachar |
| 2004/0030244 A1 | 2/2004 | Garibaldi et al. |
| 2004/0064153 A1 | 4/2004 | Creighton, IV et al. |
| 2004/0068173 A1 | 4/2004 | Viswanathan |
| 2004/0133130 A1 | 7/2004 | Ferry et al. |
| 2004/0147829 A1 | 7/2004 | Segner et al. |
| 2004/0157082 A1 | 8/2004 | Ritter et al. |
| 2004/0158972 A1 | 8/2004 | Creighton, IV et al. |
| 2004/0167385 A1* | 8/2004 | Rioux et al. ............... 600/373 |
| 2004/0186376 A1 | 9/2004 | Hogg et al. |
| 2004/0249262 A1 | 12/2004 | Werp et al. |
| 2004/0249263 A1 | 12/2004 | Creighton, IV |
| 2004/0260172 A1 | 12/2004 | Ritter et al. |
| 2004/0267106 A1 | 12/2004 | Segner et al. |
| 2005/0004585 A1 | 1/2005 | Hall et al. |
| 2005/0020911 A1 | 1/2005 | Viswanathan et al. |
| 2005/0021063 A1 | 1/2005 | Hall et al. |
| 2005/0027320 A1* | 2/2005 | Nehls et al. .................. 607/9 |
| 2005/0033162 A1 | 2/2005 | Garibaldi et al. |
| 2005/0043611 A1 | 2/2005 | Sabo et al. |
| 2005/0065435 A1 | 3/2005 | Rauch et al. |
| 2005/0096589 A1 | 5/2005 | Shachar |
| 2005/0113628 A1 | 5/2005 | Creighton, IV et al. |
| 2005/0113812 A1 | 5/2005 | Viswanathan et al. |
| 2005/0119556 A1 | 6/2005 | Gillies et al. |
| 2005/0119687 A1 | 6/2005 | Dacey, Jr. et al. |
| 2005/0182315 A1 | 8/2005 | Ritter et al. |
| 2005/0203382 A1* | 9/2005 | Govari et al. ............... 600/424 |
| 2005/0256398 A1 | 11/2005 | Hastings et al. |
| 2005/0273130 A1 | 12/2005 | Sell |
| 2006/0004382 A1 | 1/2006 | Hogg et al. |
| 2006/0009735 A1 | 1/2006 | Viswanathan et al. |
| 2006/0025676 A1 | 2/2006 | Viswanathan et al. |
| 2006/0025679 A1 | 2/2006 | Viswanathan et al. |
| 2006/0025719 A1 | 2/2006 | Viswanathan et al. |
| 2006/0036125 A1 | 2/2006 | Viswanathan et al. |
| 2006/0036163 A1 | 2/2006 | Viswanathan |
| 2006/0036213 A1 | 2/2006 | Viswanathan et al. |
| 2006/0041178 A1 | 2/2006 | Viswanathan et al. |
| 2006/0041179 A1 | 2/2006 | Viswanathan et al. |
| 2006/0041180 A1 | 2/2006 | Viswanathan et al. |
| 2006/0041181 A1 | 2/2006 | Viswanathan et al. |
| 2006/0041245 A1 | 2/2006 | Ferry et al. |
| 2006/0058646 A1 | 3/2006 | Viswanathan |
| 2006/0061445 A1 | 3/2006 | Creighton, IV et al. |
| 2006/0074297 A1 | 4/2006 | Viswanathan |
| 2006/0079745 A1 | 4/2006 | Viswanathan |
| 2006/0079812 A1 | 4/2006 | Viswanathan |
| 2006/0094956 A1 | 5/2006 | Viswanathan |
| 2006/0100505 A1 | 5/2006 | Viswanathan |
| 2006/0114088 A1 | 6/2006 | Shachar |
| 2006/0116633 A1 | 6/2006 | Shachar |
| 2006/0144407 A1 | 7/2006 | Aliberto et al. |
| 2006/0144408 A1 | 7/2006 | Ferry |
| 2006/0145799 A1 | 7/2006 | Creighton, IV |
| 2006/0270915 A1 | 11/2006 | Ritter et al. |
| 2006/0270948 A1 | 11/2006 | Viswanathan et al. |
| 2006/0278248 A1 | 12/2006 | Viswanathan |
| 2007/0016010 A1 | 1/2007 | Creighton, IV et al. |
| 2007/0016131 A1 | 1/2007 | Munger et al. |
| 2007/0019330 A1 | 1/2007 | Wolfersberger |
| 2007/0021731 A1 | 1/2007 | Garibaldi et al. |
| 2007/0021742 A1 | 1/2007 | Viswanathan |
| 2007/0021744 A1 | 1/2007 | Creighton, IV |
| 2007/0030958 A1 | 2/2007 | Munger |
| 2007/0032746 A1 | 2/2007 | Sell |
| 2007/0038064 A1 | 2/2007 | Creighton, IV |
| 2007/0038065 A1 | 2/2007 | Creighton, IV et al. |
| 2007/0038074 A1 | 2/2007 | Ritter et al. |
| 2007/0038410 A1 | 2/2007 | Tunay |
| 2007/0040670 A1 | 2/2007 | Viswanathan |
| 2007/0043455 A1 | 2/2007 | Viswanathan et al. |
| 2007/0049909 A1 | 3/2007 | Munger |
| 2007/0055124 A1 | 3/2007 | Viswanathan et al. |
| 2007/0055130 A1 | 3/2007 | Creighton, IV |
| 2007/0060829 A1 | 3/2007 | Pappone |
| 2007/0060916 A1 | 3/2007 | Pappone |
| 2007/0060962 A1 | 3/2007 | Pappone |
| 2007/0060966 A1 | 3/2007 | Pappone |
| 2007/0060992 A1 | 3/2007 | Pappone |
| 2007/0062546 A1 | 3/2007 | Viswanathan et al. |
| 2007/0062547 A1 | 3/2007 | Pappone |
| 2007/0073288 A1 | 3/2007 | Hall et al. |
| 2007/0088197 A1 | 4/2007 | Garibaldi et al. |
| 2007/0135804 A1 | 6/2007 | Ritter |
| 2007/0137656 A1 | 6/2007 | Viswanathan |
| 2007/0146106 A1 | 6/2007 | Creighton, IV |
| 2007/0149946 A1 | 6/2007 | Viswanathan |
| 2007/0161882 A1 | 7/2007 | Pappone |

| | | | | | |
|---|---|---|---|---|---|
| 2007/0167720 A1 | 7/2007 | Viswanathan | 2007/0197901 A1 | 8/2007 | Viswanathan |
| 2007/0179492 A1 | 8/2007 | Pappone | 2007/0197906 A1 | 8/2007 | Ritter |
| 2007/0197899 A1 | 8/2007 | Ritter et al. | * cited by examiner | | |

NAVIGATION USING SENSED PHYSIOLOGICAL DATA AS FEEDBACK

CROSS-REFERENCE TO RELATED APPLICATIONS

This application claims the benefit of U.S. provisional patent application Ser. No. 60/642,853 filed Jan. 11, 2005, the entire disclosure of which is incorporated herein by reference.

BACKGROUND OF THE INVENTION

Cardiac arrhythmias are a form of cardiac disease where the electrical activity of the heart is disrupted, often due to the takeover of signal generation by abnormal excitation nodes.

Cardiac arrhythmia may be treated through minimally invasive interventions such as catheter ablation, where catheters navigate a set of electrodes (often 3-8 electrodes) intravascularly into the relevant chambers of the heart, and monitor electrical signal activation times and propagation to thereby identify location points of focal arrhythmias, for example Supraventricular Tachycardia (e.g, SVT). An electro-physiological study is performed to record the activation sequence at target locations of the heart, to determine the arrhythmia mechanism. Such mapping may then be used to identify location points within the heart that are part of the tachycardia or arrhythmia mechanism, but not part of the normal cardiac conduction system. Such location points are then rendered electrically inactive by ablating the point, typically by Radio Frequency ablation. The electrophysiological study may also record blood flow velocity, to determine areas of disrupted blood flow caused by poorly coordinated pumping of the heart chambers. Where the heart valve chambers are fluttering, vortices will occur at certain regions while other regions will have streamline blood flow. The electrophysiological catheter is useful in assisting in the diagnosis and treatment of such conditions. Recent advancements have also resulted in automated remote navigation systems that can drive catheter placement with a great deal of precision, more specifically magnetic navigation systems.

SUMMARY OF THE INVENTION

Embodiments of the systems and methods of the present invention advance the art of remote surgical navigation by combining diagnosis with navigation and therapy, using a minimal number of devices. In one embodiment of the present invention, a system is provided for treatment of arrhythmia that comprises an electrophysiological catheter having at least one electrode for sensing intra-cardiac wave front activation signals on a tissue surface, a navigation system for guiding the distal end of the catheter to a number of locations for sensing intra-cardiac activation signals along the wall of a subject body's heart, and an ECG recording system for recording the local intra-cardiac signal data for each of the locations. The system further comprises a computer for determining the direction of propagation of the wave front with respect to time from the intra-cardiac activation signals corresponding to the location points. From the direction of propagation of the wave front, the computer may calculate a new location point in the direction of the source of the wave front for advancing the catheter to, where intra-cardiac activation data may be used with at least two of the prior locations for further evaluation of the wave front direction.

In one aspect of the present invention, a method is provided for determining the movements of the catheter towards a focal arrhythmia for ablation. A method is provided in combination with a navigation system, a localization system, and an algorithm for directing the movement of the catheter. The method comprises navigating the distal end of the catheter to sense intra-cardiac activation signals at a number of locations on the wall of a subject body's heart, recording the local intra-cardiac signal data for the minimum number of locations, and determining the direction of propagation of the wave from with respect to time from the location points using the algorithm. The method further comprises calculating a new location point in the direction of the source of the wave front using the algorithm, for use with at least two of the prior locations for further evaluation of the wave front direction, iteratively repeating the step of determining the direction of propagation to obtain the earliest activation location of the wave front, and responsively navigating the distal tip of the catheter to the earliest activation location for providing medical treatment.

In another aspect of the present invention, a means is provided for determining patterns of disrupted blood flow caused by poorly coordinated pumping of heart chambers. The means for determining blood flow comprises a fluid velocity sensing means located on the tip of the electrophysiological catheter, for use in diagnosis and treatment of arrhythmia. In one embodiment of the present invention, the one or more fluid velocity sensors are capable of measuring temperature changes across a region of the sensor to determine relative changes in fluid velocity, as well as alignment of the fluid flow direction with respect to the temperature change. The one or more fluid velocity sensors are oriented relative to the catheter so as to provide for determining the component of direction of the fluid velocity relative to the catheter tip. In another embodiment of the present invention, one or more Doppler fluid velocity sensing means are located on the tip of the electrophysiological catheter. The one or more Doppler fluid velocity sensing means comprise a transmitter for transmitting a high frequency sound wave into the fluid, and an antenna that detects a frequency shift of the reflected wave from the fluid particles to determine the fluid velocity. In both embodiments, the one or more fluid velocity sensors are oriented relative to the catheter so as to provide for determining the component of direction of the fluid velocity relative to the catheter tip.

In yet another aspect of the present invention, a preferred embodiment of a method for controlling the navigation of a medical device within a subject body to sense an electrophysiological property is also provided. The method may be used to navigate a medical device comprising one or more physiological sensing means to a plurality of regions within a subject body, for sensing the value or relative change in value of a sensed physiological property such as an electrical signal, conductivity, temperature, or fluid velocity and direction as previously disclosed. The method of controlling a remote navigation system to navigate a medical device in an operating region in a subject comprises operating the remote navigation system to bring a sensor carried on a medical device successively into a plurality of locations in a predetermined pattern, and using the sensor to sense a physiological property of the subject in each location. At least once thereafter, the method operates the remote navigation system to bring a sensor carried on a medical device successively into a series of locations in a predetermined pattern relative to at least one location selected from the predetermined pattern in the immediately preceding step based upon the sensed physiological property value, and uses the sensor to sense the physiological property in each location. The method automatically determines the location of a local extreme value of the sensed physiological property, and may be selectively used to locate a maximum value of the sensed physiological property or a minimum of the sensed physiological property.

DETAILED DESCRIPTION OF THE INVENTION

Embodiments of the systems and methods of the present invention are provided that comprise various electrophysiological sensors disposed on the tip of a catheter for sensing and recording local activity of tissues or fluid flow within the body. The various embodiments of the present invention are capable of measuring local electrical activity, temperature, fluid velocity and fluid flow direction in a local area within a subject body using a minimal number of devices.

Figure 1:
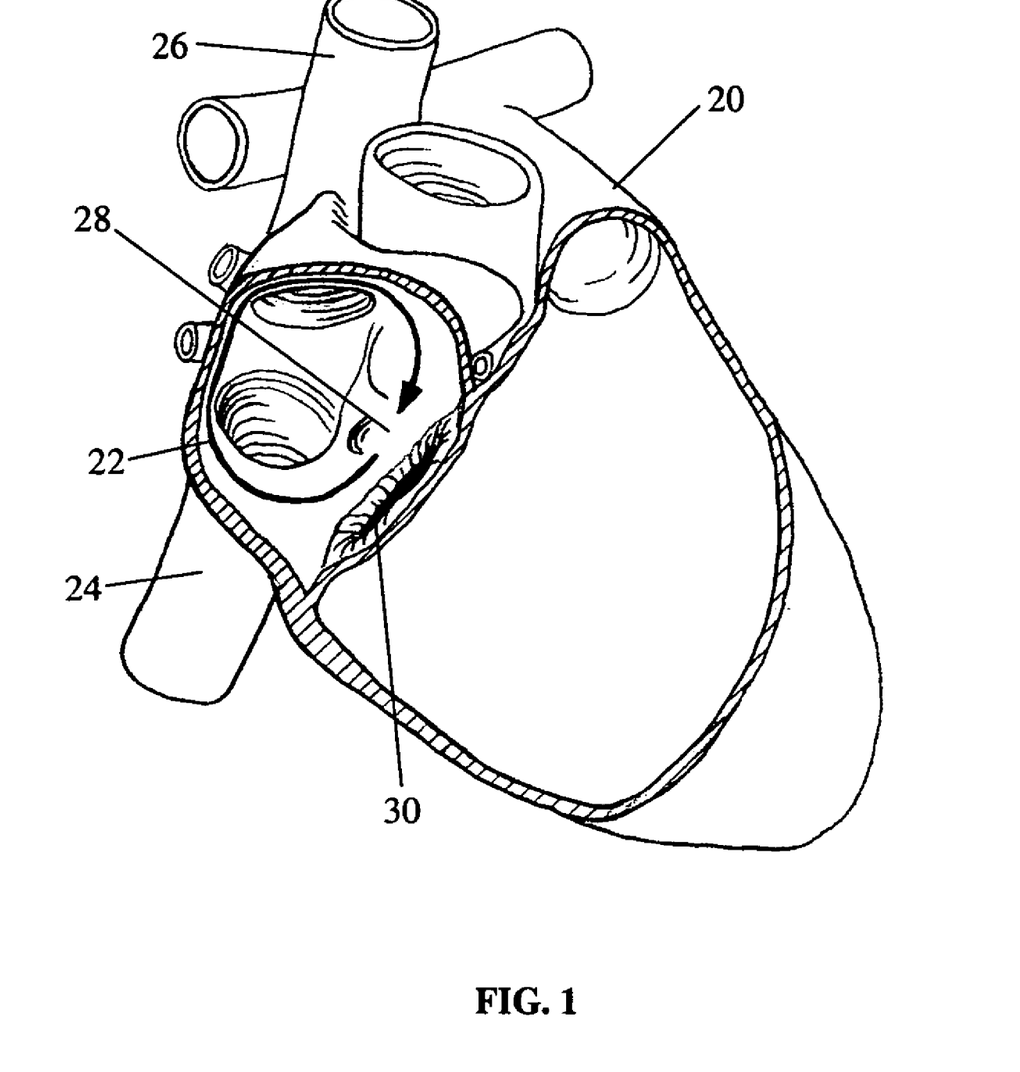
FIG. 1 is a cut away view of a heart showing a re-entry circuit within the right atria and a possible target area for ablation to render the re-entry mechanism inactive.

In a preferred embodiment of the present invention, a system and method are provided for measuring and recording various points in a region of a patient's heart for mapping electrophysiological activity of the tissue, and for determining a target location for catheter ablation to correct an arrhythmia mechanism. The arrhythmia mechanism of an atrioventricular re-entry tachycardias may be established where an electrical wave front occurs within the heart that generates a re-entry circuit. In the cutaway of a heart 20 in FIG. 1, an example of a re-entry circuit is generally shown as a circular electrical pathway 22 within the right atrium around the inferior vena cava 24 and superior vena cava 26. A possible target 28 for atrial ablation, for example, could be near the isthmus between the tricuspid valve 30 and the inferior vena cava 24. Ablation would render the location electrically inactive, and would interrupt the electrical pathway of the re-entry circuit. Atrioventricular Nodal Re-entry Tachycardia is another arrhythmia mechanism that is established where both a fast and slow conduction pathways into the atrioventricular node exist. Atrial flutter and Focal Atrial Tachycardia are yet further re-entry mechanisms in which the passage of the activation wave front around the atrium establishes re-polarization of the ventricle before the wave front completes one circuit. The present invention provides a method for evaluating such various arrhythmia mechanisms and determining the source or focal point of the arrhythmia to be treated. The method described herein involves using a single catheter to measure and record intracardiac electrical activity in a small local region, identify the direction of signal propagation of the wave front of intracardiac activity from these measurements, and navigate the catheter in the appropriate direction towards the source of the wave front. Once identified, such electrical signal sources that are not part of the normal cardiac conduction system can be removed by catheter ablation techniques such as Radio Frequency (RF) ablation, where electrical energy is delivered through the tip electrode of the catheter in order to locally destroy abnormal tissue.

In one preferred embodiment in accordance with the present invention, a system for treatment of arrhythmia is provided that comprises a catheter having at least one electrode for sensing intra-cardiac wave front activation signals on a tissue surface, and a navigation system for guiding the distal end of the catheter to a minimum number of locations to sense intra-cardiac activation signals along the endocardial wall of a subject's heart. Navigation of the catheter may be performed by a magnetic navigation system or any other navigation system suitable for guiding a catheter within a subject body. An ElectroPhysiology ECG recording system is used for recording the location the local intra-cardiac electrical signal data corresponding to the minimum number of locations. In one preferred embodiment, a localization system is used to record catheter tip location data together with intra-cardiac electrical signal data. The system may also include a fluoroscopic imaging system for obtaining images and location points of the catheter within the body during the surgical procedure. In an alternate embodiment, fluoro-localization is used to record three dimensional catheter tip location data by manually marking on corresponding points in at least two fluoro images.

In a preferred embodiment, the catheter may be a magnetically navigable catheter, which may be advanced through the vasculature in a selected direction by pushing the proximal end of the catheter, and by deflecting the distal end of the catheter by an applied magnetic field to gain entry to a vessel branch. The distal end of the catheter may comprise a radio-opaque material useful for viewing in an X-ray or fluoroscopic imaging system, and one or more magnetic elements which can be deflected to align with an applied magnetic field external to the subject body of a patient. One such navigation system, for example, is the Stereotaxis Niobe™ magnetic navigation system, which can apply an external magnetic field of about 0.08 Tesla within the subject in any direction in order to suitably orient or steer the catheter. In alternate embodiments, other actuation schemes such as mechanical, electrostrictive, hydraulic or other methods could be used to steer or deflect the catheter in order to navigate it.

The system further comprises a computer for determining the regional direction of propagation of the wave front from the intra-cardiac signal data corresponding to the location points. By determining the direction of propagation of the wave front, the computer calculates a new location for advancing the catheter in the direction of the source of the wave front, where intra-cardiac signal data may be used with at least two of the prior locations for further evaluation and adjustment of the estimated wave front direction. The computer may execute an algorithm for iteratively repeating the above progression to determine the earliest activation location or source of the wave front, and responsively navigating the distal tip of the catheter to the earliest activation location for medical treatment.

The preferred embodiment further comprises a method for determining the point of earliest activation of a local wave front associated with focal atrial tachycardia. The method includes the step of determining the direction of propagation of the wave front from an analysis of signal delays or signal arrival times in the intra-cardiac signal data corresponding to the location points. By determining the direction of the propagation of the wave front, the method calculates a new location for advancing the catheter in the direction of the source of the wave front, where intra-cardiac signal data may be used with at least two of the prior locations for further evaluation or estimation of the wave front propagation direction. The method repeats the iterative progression to determine the earliest activation location of the wave front and to responsively navigate the distal tip of the catheter to the earliest intra-cardiac activation location for medical treatment.

The system and method may automatically determine the location of a focal point of arrhythmia or atrial tachycardia re-entry mechanism where unpolarized intra-cardiac activation is initiated, and may automatically advance the catheter to the location for ablation treatment. The method may also be used to perform an electrophysiological study for generating an electro-anatomical map of the heart tissue. Such atrial tachycardia re-entry or other cardiac arrhythmia mechanisms are established by lines of conduction that can be visualized using mapping systems that can characterize and predict focal points. The advantages of the methods used in the present invention to evaluate measured local intracardiac activation data and to responsively determine the propagation of the wave front of intracardiac activation for moving the mapping/ablation catheter to a desired location for ablation will become apparent from the following detailed description of the method.

Step 1

The catheter tip is positioned at three locations on the wall of the heart chamber and the electrical signals recorded at each of these locations. The locations are preferably mutually separated by separations in the range 5 mm-20 mm and more preferably in the range 5 mm-15 mm. An ECG system (ideally outputting data to the navigation system) records local intracardiac signal data at each of these locations $p_1$, $p_2$, and $p_3$. At $p_1$, the ECG data is recorded for about 3-20 cycles to determine the periodicity T of the signal. The position $\vec{X}p_1$, can be determined, for example by fluoro-localization.

Step 2

Figure 2:
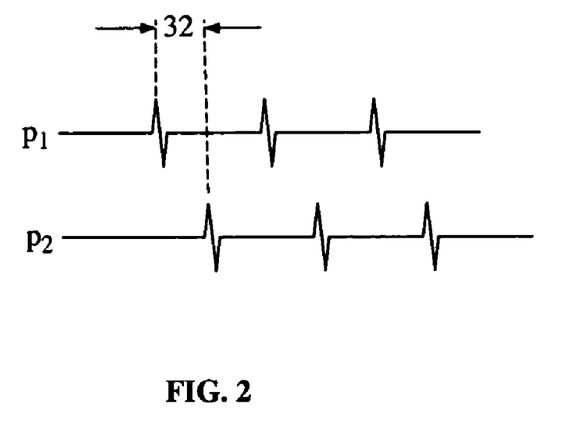
FIG. 2 is an illustration of the difference in phase of ECG signals at points $p_1$ and $p_2$.

The catheter is moved to location $p_2$, and its position $\vec{X}p_2$ is determined, for example by fluoro-localization. The electrical signal is recorded and its phase difference with respect to the signal at $p_1$, is measured. FIG. 2 illustrates the phase difference 32 of signals at $p_1$, and $p_2$. If the signal (peak) at $p_2$ is measured at time $\tau$, $\Delta_2=(\tau-NT)$ where N is the largest integer such that $\Delta_2$ is positive. If $\Delta_2 > T/2$, define $a'=-(T-\Delta_2)$, else define $a'=\Delta_2$; $a'$ is the phase difference at $p_2$.

The catheter is then moved to location $p_3$, and its position $\vec{X}p_3$ is determined, for example by fluoro-localization. The electrical signal is recorded, and its phase difference $b'$ is determined.

Step 3

The points are relabeled as needed such that $p_1$, is the point of earliest activation, i.e., $a'$ and $b'$ (phase differences at the other 2 points with respect to $p_1$,) are both positive, and are hereinafter referred to as a and b instead of $a'$ and $b'$.

Figure 3:
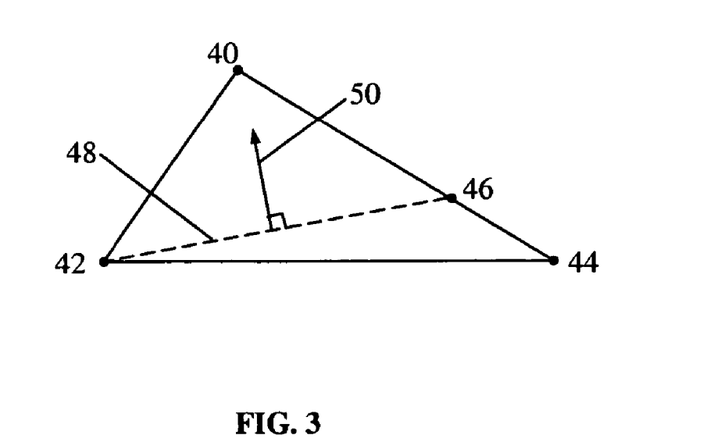
FIG. 3 is an illustration of a number of location points of intra-cardiac activity having phase signal differences, and a corresponding direction of wave front propagation.

The triangle formed by points $p_1$, (40), $p_2$, (42), and $p_3$ (44) is shown in FIG. 3. The three triangle points $p_1$, (t=0), $p_2$, (t=a), and $p_3$ (t=b) all have associated time or propagation delays relative to the other points. This is a small (local) triangle, and therefore the time (propagation) delays within this triangle may be linearly interpolated with little error. Isochrones (contours of equal propagation time) within this triangle represent the local wave front; the direction of propagation is normal to this wave front. Referring to FIG. 3, where b>a (no loss of generality), the isochrone passing through point $\vec{X}_2$ (42) is the dotted line 48, intersecting edge $x_1$-$x_3$ of the triangle at a point $\vec{X}_0$ (46), such that $$\vec{x}_0 = \vec{x}_1 + \frac{a}{b}(\vec{x}_3 - \vec{x}_1)$$

(since propagation delays are linearly interpolated within the triangle). The vector $\vec{l} = (\vec{x}_0 - \vec{x}_2)$ is therefore along the isochronal direction $\vec{n}$ (or at equal time propagation). Since the propagation direction 50 must be perpendicular to this, $$\vec{n} \cdot \vec{l} = o, \text{ or } \vec{n} \bullet (\vec{\chi}_0 - \vec{\chi}_x) = o. \quad (1)$$

Therefore, $$\vec{n} = \alpha \vec{u}_1 + \beta \vec{u}_2 \quad (2)$$

where $$\vec{u}_2 = \frac{(\vec{\chi}_1 - \vec{\chi}_s)}{|\vec{\chi}_1 - \vec{\chi}_2|}$$

$$\text{and } \vec{u}_2 = \frac{(\vec{\chi}_3 - \vec{\chi}_x)}{|\vec{\chi}_3 - \vec{\chi}|_2} \quad (3)$$

$\vec{n}$ is a unit vector, so we have $$\alpha^2 + \beta^2 + 2\alpha\beta \cos \Theta = 1 \quad (4)$$

where $\cos o = \vec{u}_1 \cdot \vec{u}_2$.

From equations (1) and (2):

$$\vec{n} \cdot (\vec{\chi}_o - \vec{\chi}_x) = 0 \text{ or}$$

$$(\alpha \vec{u}_1 + \beta u_2) \cdot [b(\vec{x}_1 - \vec{x}_x) + a(\vec{x}_3 - \vec{x}_1)] = 0$$

or $$\alpha[b\vec{u}_1 \cdot (\vec{x}_1 - \vec{x}_2) + a\vec{u}_1 \cdot (\vec{x}_3 - \vec{x}_1)] + \beta[b\vec{u}_2 \cdot (\vec{x}_1 - \vec{x}_2) + a\vec{u}_2 \cdot (\vec{x}_3 - \vec{x}_1)] = 0 \quad (5)$$

Equations (4) and (5), can be solved for $\alpha$ and $\beta$, and thus $\vec{n}$ can be determined (pick the sign of $\vec{n}$ such that $\vec{n}$ points towards $\vec{x}_1$, or such that n has positive dot product with the vector $(x_1 - (x_0 + x_2)/2)$).

Step 4

Once $\vec{n}$ (the local reverse propagation direction) is determined, starting at $\vec{x}_1$, a new point $\vec{y}_1' = A\vec{n} + \vec{x}_1$ is defined where A is a step size in the range 5 mm-20 mm. $\vec{y}_1'$ is defined as a new target for the catheter; because the wall surface is curved, target navigation of the catheter (with suitable control actuations applied) will actually take the tip to a location $\vec{y}_1$. A new triangle $O_2$ is formed by the points $\vec{y}_1$ and the 2 points (from triangle $O_1$) that are closest to it. The process is iteratively repeated to get a new local propagation direction in triangle $O_2$, as long as the activation time at point $\vec{y}_1$ is earlier than that of the other 2 points in $O_2$. If the activation time at $\vec{y}_1$, is later than that of at least one of the other 2 points, a reduced step is taken:

$$\text{Define } \vec{z}_1' = \frac{A}{2}\vec{n} + \vec{x}_1$$

and navigate the catheter to a (real) wall location $\vec{z}_1$, etc.

Step 5

In a relatively small number of steps/iteration, the focal point of the arrhythmia may thus be found and the catheter will have been placed there. Ablative therapy may be performed to eliminate the source of the arrhythmia.

It is worth noting that these methods may be generalized to multi-focal arrhythmias by looking for double periodicities and other signal features, such that multiple isochrones may be tracked locally to arrive at multiple foci. Likewise more than one catheter may be used in combination for diagnosis and navigation. The remote navigation system could be used with a localization system with location feedback, or with a registered pre-operative or other anatomical data. In the latter case, a suitably modified stepping point $\vec{y}_1$ etc. may be directly defined on the (curved) heart surfaces so that a stepped path is defined on the curved surface, minimizing the need for repeated fluoro localization. Although fluoro-localization has been described in the example detailed above, in the case where real-time location data is available from a device localization system, fluro-localization is not needed, again minimizing the need for repeated user interaction. In an alternate embodiment, catheter tip location could be estimated or evaluated from a knowledge of actuation control variables from the navigation system and a computational device model that predicts tip location based on the actuation controls. Varying levels of automation thus are possible depending a system integration and availability of anatomical and/or catheter location data.

It should be noted that the above preferred embodiment useful for sensing electrical activity may also employed to sense conductivity. A low voltage signal may be applied to the at least one electrode, and the current conducted through the tissue may be measured and recorded for enabling mapping of conductivity of a tissue surface. The catheter or medical device may be navigated to bring the electrode successively into a plurality of locations in a predetermined pattern, to sense the conductivity of each location. At least once thereafter, the medical device may be navigated to bring the electrode successively into further locations in a predetermined pattern relative to at least one location selected from the immediately preceding plurality of locations. An algorithm may be used to automatically operate the navigation system to bring the sensor to a series of locations in a predetermined pattern, to guide the medical device to a local extreme of a sensed conductivity, such as an area of minimum electrical conductivity. Such an algorithm may utilized the method disclosed above for automatically navigating the medical device in a predetermined pattern to locate a region having a local extreme.

Figure 4:
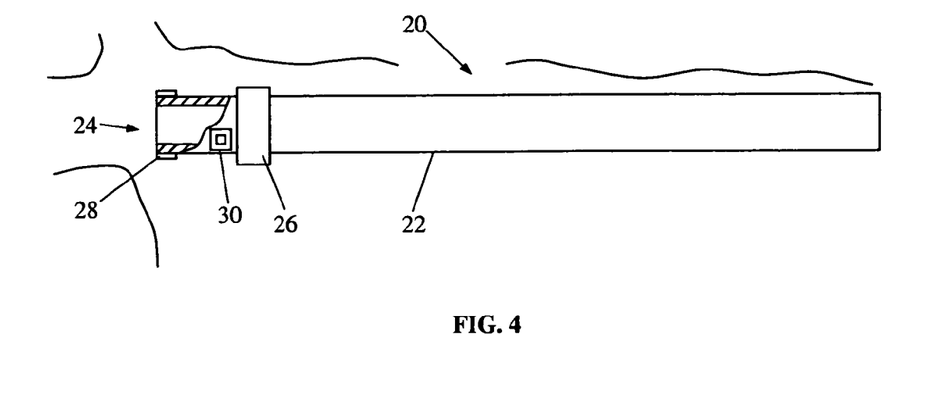
FIG. 4 is a side view of one embodiment of an electrophysiological catheter having a fluid velocity sensing means according to the principles of the present invention.

In another embodiment of the present invention, an electrophysiological catheter 20 is provided that further comprises one or more fluid velocity sensing means disposed on the tip of the catheter. As shown in FIG. 4, the catheter 20 comprises a tubular element 22 having a proximal end and a distal end 24. The distal end of the catheter comprises at least one magnetically responsive element 26 for enabling navigation of the distal end, and also comprises one or more electrodes 28. One or more fluid velocity sensing means 30 may be utilized for sensing relative changes in velocity of a fluid flowing across the sensing means. The one or more fluid velocity sensors are capable of measuring temperature changes across a region of the sensor to determine relative changes in fluid velocity, as well as alignment of the fluid flow direction with respect to the temperature change. The one or more fluid velocity sensors are oriented relative to the catheter so as to provide for determining the component of direction of the fluid velocity relative to the catheter tip. The current conducted through the tissue may be measured and recorded for enabling mapping of conductivity of a tissue surface. The fluid velocity sensing means comprises a micromachined structure having a heater that measures temperature drop across a region to determine the relative change in fluid velocity across the heater. Such a device need not be calibrated for absolute velocity in this application, but instead would determine relative values at appropriate locations within the subject body. The heater comprises a homogeniously heated segmented heater having a plurality of heated segments forming a generally square shape, for enabling the detection of a relative temperature difference between corresponding segments. The plurality of segments provide for determining the flow direction corresponding to the sensed fluid velocity across the heater. By orienting one or more fluid velocity sensing means of this type on the tip of the catheter, the component of direction of the fluid velocity relative to the catheter could be determined.

The catheter or medical device may be navigated to bring the fluid velocity sensing means successively into a plurality of locations in a predetermined pattern, to sense the fluid velocity at each location. At least once thereafter, the medical device may be navigated to bring the fluid velocity sensing means successively into further locations in a predetermined pattern relative to at least one location selected from the immediately preceding plurality of locations. An algorithm may be used to automatically operate the navigation system to bring the fluid velocity sensing means to a series of locations in a predetermined pattern, to guide the medical device to a local extreme of a sensed fluid velocity, such as an area of minimum fluid velocity or a vortices in the blood flow. The fluid velocity sensing means could also be used to sense local maximums of fluid velocity such as regions of streamline blood flow through the chambers of the heart. The mapping of such velocity data is useful in assisting in the diagnosis of medical conditions such as cardiac arrhythmia. The algorithm utilized may employ the method disclosed above for automatically navigating the medical device in a predetermined pattern to locate a region having a local extreme.

This embodiment comprising a fluid sensing means may also be used to sense the temperature of a location as well. The homogeniously heated segmented heater establishes a base temperature, which may be increased or decreased by the surrounding tissues it comes into contact with. Thus, the above sensing means is capable of sensing a temperature drop across the surface as well as changes in absolute temperature of the homogeniously heated sensor. This sensing means may also be used to sense relative changes in temperature from location to location.

In yet another embodiment of the present invention, an electrophysiological catheter is provided that further comprises one or more Doppler fluid velocity sensing means disposed on the tip of the catheter, for sensing relative changes in fluid velocity across the sensing means. The one or more Doppler fluid velocity sensing means are capable of measuring frequency shifts in a wave signal to determine relative changes in fluid velocity, as well as alignment of the fluid flow direction with respect to the sensing means. The one or more Doppler fluid velocity sensing means comprise a transmitter for transmitting a high frequency sound wave into the fluid, and an antenna that detects a frequency shift of the reflected wave from the fluid particles to determine the fluid velocity. Electrical connections for the micro-transmitter and antenna may be disposed within the catheter or medical device to provide for measuring and recording of the sensed fluid velocity. The one or more Doppler fluid velocity sensors are oriented relative to the catheter so as to provide for determining the component of direction of the fluid velocity relative to the catheter tip. By orienting one or more fluid velocity sensing means of this type on the tip of the catheter, the component of direction of the fluid velocity relative to the catheter could be determined.

A preferred embodiment of a method of controlling the navigation of a medical device within a subject body to sense an electrophysiological property is also provided. The method may be used to navigate a medical device comprising one or more physiological sensing means to a plurality of regions within a subject body, for sensing the value or relative change in value of a sensed physiological property such as an electrical signal, conductivity, temperature, or fluid velocity and direction as previously disclosed. The method of controlling a remote navigation system to navigate a medical device in an operating region in a subject comprises operating the remote navigation system to bring a sensor carried on a medical device successively into a plurality of locations in a predetermined pattern, and using the sensor to sense a physiological property of the subject in each location. At least once thereafter, the method operates the remote navigation system to bring a sensor carried on a medical device successively into a series of locations in a predetermined pattern relative to at least one location selected from the predetermined pattern in the immediately preceding step based upon the sensed physiological property value, and uses the sensor to sense the physiological property in each location. The method automatically determines the location of a local extreme value of the sensed physiological property, and may be selectively used to locate a maximum value of the sensed physiological property or a minimum of the sensed physiological property. Some embodiments of a medical device for sensing a physiological property may be capable of sensing more than one property, and may be employed to sense any one of a magnitude of an electrical signal, a conductivity, a temperature, a fluid flow rate or a fluid velocity, or a range of motion of a surface.

What is claimed is:

1. A method of controlling a remote navigation system to navigate a medical device in an operating region in a subject, the method comprising:
   operating the remote navigation system to bring a sensor carried on a medical device successively into a plurality of locations in a predetermined pattern, and using the sensor to sense a physiological property of the subject in each location; and
   at least once thereafter, operating the remote navigation system to bring a sensor carried on a medical device successively into a series of locations in a predetermined pattern relative to at least one location selected from the predetermined pattern in the immediately preceding step based upon the sensed physiological property, and using the sensor to sense the physiological property in each location.

2. The method according to claim 1, wherein the method comprises automatically successively operating the remote navigation system to bring the sensor carried on the medical device to a position determined by an algorithm using at least one previously sensed physiological property and corresponding location as an input, and sensing the physiological property in the location.

3. The method according to claim 1 wherein the sensed physiological property is the magnitude of an electrical signal.

4. The method according to claim 1 wherein the sensed physiological property is the timing of an electrical signal.

5. The method according to claim 1 wherein the sensed physiological property is temperature.

6. The method according to claim 1 wherein the sensed physiological property is range of motion of a surface.

7. The method according to claim 1 wherein the sensed physiological property is conductivity.

8. The method according to claim 1 wherein the sensed physiological property is a flow rate.

9. The method according to claim 1 wherein the sensed physiological property is a fluid velocity.

10. A method of automatically finding the location of a local extreme of a sensed physiological property, the method comprising:
    operating a remote navigation system to bring a sensor carried on a medical device successively into a plurality of locations in a predetermined pattern, and using the sensor to sense a physiological property of the subject in each location; and
    at least once thereafter, operating the remote navigation system to bring a sensor carried on a medical device successively into a series of locations in a predetermined pattern relative to at least one location selected from the predetermined pattern in the immediately preceding step based upon the sensed value physiological property, and using the sensor to sense the physiological property in each location to identify the local extreme of the sensed physiological property.

11. The method according to claim 10 wherein the local extreme of the sensed physiological property is a maximum of the sensed physiological property.

12. The method according to claim 10 wherein the local extreme of the sensed physiological property is a minimum of the sensed physiological property.

13. A method of automatically finding the location of a local extreme of a sensed physiological property in an operating region in a subject, the method comprising:
    automatically successively operating a remote navigation system to bring a sensor carried on a medical device to a position determined by an algorithm using at least one previously sensed physiological value and corresponding location as an input, and sensing the physiological property in the location.

14. The method according to claim 13 wherein the local extreme of the sensed physiological property is a maximum of the sensed physiological property.

15. The method according to claim 13 wherein the local extreme of the sensed physiological property is a minimum of the sensed physiological property.

* * * * *